(12) United States Patent
Rattay et al.

(10) Patent No.: US 9,618,492 B2
(45) Date of Patent: Apr. 11, 2017

(54) SENSOR HAVING A HOUSING SEAL MADE OF SYNTHETIC RUBBERS HAVING DIFFERING ELASTICITY

(75) Inventors: Bernd Rattay, Ditzingen (DE); Jens Schneider, Leonberg (DE); Guido Soyez, Ludwigsburg (DE); Arno Clauss, Lauffen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 198 days.

(21) Appl. No.: 14/343,539

(22) PCT Filed: Jul. 23, 2012

(86) PCT No.: PCT/EP2012/064395
§ 371 (c)(1),
(2), (4) Date: Jun. 23, 2014

(87) PCT Pub. No.: WO2013/034353
PCT Pub. Date: Mar. 14, 2013

(65) Prior Publication Data
US 2014/0326069 A1 Nov. 6, 2014

(30) Foreign Application Priority Data
Sep. 7, 2011 (DE) .................... 10 2011 082 260

(51) Int. Cl.
*G01D 11/24* (2006.01)
*G01N 33/00* (2006.01)
*G01N 27/406* (2006.01)

(52) U.S. Cl.
CPC ....... *G01N 33/0036* (2013.01); *G01D 11/245* (2013.01); *G01N 27/4062* (2013.01)

(58) Field of Classification Search
CPC .............................. G01D 11/24; G01D 11/245
(Continued)

(56) References Cited

U.S. PATENT DOCUMENTS 4,141,813 A * 2/1979 Kita .................... G01N 27/4078
204/428
4,320,378 A * 3/1982 Taniguchi .......... G01N 27/4077
338/229

(Continued)

FOREIGN PATENT DOCUMENTS

CN 1158164 A 8/1997
CN 1197512 A 10/1998
(Continued)

OTHER PUBLICATIONS

International Search Report, PCT International Application No. PCT/EP2012/064395, dated Sep. 24, 2012.
(Continued)

*Primary Examiner* — Lisa Caputo
*Assistant Examiner* — Jamel Williams
(74) *Attorney, Agent, or Firm* — Gerard Messina

(57) ABSTRACT

A sensor for determining at least one property of a measuring gas in a measuring gas space is provided. The sensor has a housing which includes a housing opening. At least one connection cable is led from the housing through the housing opening. The sensor further includes at least one sealing body, in particular a grommet, the sealing body at least partially enclosing the connection cable. The sealing body has at least one first section and at least one second section, the first section having a higher deformability than the second section.

23 Claims, 3 Drawing Sheets

(58) Field of Classification Search
USPC .......................................................... 73/431
See application file for complete search history.

(56) References Cited

U.S. PATENT DOCUMENTS

| | | | | |
|---|---|---|---|---|
| 4,868,967 | A * | 9/1989 | Holt | F16L 5/02 |
| | | | | 174/135 |
| 5,070,597 | A * | 12/1991 | Holt | F16L 5/02 |
| | | | | 138/103 |
| 5,246,562 | A | 9/1993 | Weyl et al. | |
| 5,525,073 | A * | 6/1996 | Sampson | H02G 15/18 |
| | | | | 439/358 |
| 2011/0210521 | A1 | 9/2011 | Warren et al. | |
| 2011/0307214 | A1* | 12/2011 | Saitou | G01B 7/18 |
| | | | | 702/155 |
| 2012/0318557 | A1* | 12/2012 | Iwasaki | C08K 5/0025 |
| | | | | 174/113 C |
| 2015/0134039 | A1* | 5/2015 | Marzano | A61N 1/3754 |
| | | | | 607/116 |

FOREIGN PATENT DOCUMENTS

| | | | |
|---|---|---|---|
| CN | 1349282 A | 5/2002 | |
| CN | 101095202 A | 12/2007 | |
| CN | 101208548 A | 6/2008 | |
| CN | 201326835 Y | 10/2009 | |
| CN | 101728800 A | 6/2010 | |
| DE | 40 34 072 | 4/1992 | |
| DE | 4034072 A1 * | 4/1992 | ......... G01N 27/4077 |
| DE | 101 21 890 | 11/2002 | |
| DE | 10121890 A1 * | 11/2002 | ......... H01R 13/5205 |
| EP | 2 192 403 | 6/2010 | |
| TW | 345768 B | 7/2011 | |

OTHER PUBLICATIONS

Robert Bosch GmbH, "Sensoren im Kraftfahrzeug," 1$^{st}$ Edition, pp. 160-165, 2010.

* cited by examiner

SENSOR HAVING A HOUSING SEAL MADE OF SYNTHETIC RUBBERS HAVING DIFFERING ELASTICITY

BACKGROUND INFORMATION

A number of sensors and methods for determining at least one property of a measuring gas in a measuring gas space are available. In principle, this may involve arbitrary physical and/or chemical properties of the gas, whereby one or multiple properties may be detected. The present invention is described below in particular with reference to a qualitative and/or quantitative detection of a gas component of the gas, in particular with reference to a detection of an oxygen content in the gas. The oxygen content may be detected, for example, in the form of a partial pressure and/or in the form of a percentage. Alternatively or in addition, other properties of the gas may also be detected, such as the temperature of the gas, for example.

Such sensors may, for example, also be designed as so-called lambda sensors, as are described for example, in Konrad Reif (publisher): Sensoren im Kraftfahrzeug, $1^{st}$ edition, 2010, pp. 160-165. With broadband and binary lambda sensors, in particular with planar broadband and binary lambda sensors, it is possible for example to determine the oxygen concentration in the exhaust gas at one point or in a large area, and thereby deduce the air-fuel ratio in the combustion chamber. Alternatively, the sensor may also be designed as a finger-type sensor. The air ratio $\lambda$ describes this air-fuel ratio.

Sensors of this type normally have a housing which includes a housing opening through which the connection cables are led out, and a sealing body situated in the housing opening through which the connection cables extend. The sealing body is a stopper made of a homogenous elastomeric mass through which the connection cables are guided and which is subsequently caulked in a section of the housing designed as a metal sleeve. This is described, for example, in European Patent No. EP 2 192 403 A1. Heavy demands in terms of temperature and water and gas tightness are placed on such sensors and in particular on the cable outlet. To adjust the elastic properties which result in an improved processing and improved sealing behavior, plasticizers are added to the elastomer and homogenously distributed in the elastomeric mass during the manufacture of the sealing body.

Despite the numerous advantages of the conventional sensors, they still have potential for improvement. Thus, for example, a high proportion of plasticizers in the elastomeric mass creates a high elasticity, good processability in new condition, good sealing capability in particular in the area of the grommet, but also increased material discharge during thermal aging with accompanying shrinkage and embrittlement. This may result in the formation of critical leakage paths in the cable outlet of the sensor. Conversely, a lower proportion of plasticizers in the elastomeric mass leads to poorer processability and poorer sealing capabilities, but to improved aging behavior, since under thermal load only few volatile organic components are discharged with correspondingly little change in the properties of the sealing body.

SUMMARY

Therefore, an example sensor for determining at least one property of a measuring gas in a measuring gas space and an example method for manufacturing the same are provided, which at least largely avoid the disadvantages of conventional sensors.

The sensor includes a housing which has a housing opening, at least one connection cable being led from the housing through the housing opening. The sensor also has at least one sealing body, in particular a grommet, the connection cable being at least partially enclosed by the sealing body. The sealing body includes at least one first section and at least one second section, the first section having a higher deformability than the second section.

The deformability may involve an elasticity and/or a plasticity and/or a compressibility. The sealing body may be situated at least partially in the housing opening. The sealing body may include at least one plastic material having at least one plasticizer, the first section and the second section having a different proportion of plasticizer in the plastic material, the first section in particular having a higher proportion of plasticizer than the second section. The plastic material may contain the at least one plasticizer in a proportion of 0.1% to 15% by weight, preferably 0.25% to 12.5% by weight and even more preferably 0.5% to 10% by weight, for example 5% by weight. The at least one plasticizer may contain fluorine. The plastic material may include at least one elastomer. The elastomer may be selected from the group composed of: fluororubber, in particular fluororubber having a fluorine content of at least 50% by weight, preferably at least 55% by weight and even more preferably at least 60% by weight, for example, 65% by weight; perfluororubber, in particular perfluororubber having a fluorine content of at least 50% by weight, preferably at least 55% by weight and even more preferably at least 60% by weight, for example, 65% by weight. The first section may surround the at least one connection cable. The second section may be situated coaxially relative to the first section. The second section may be situated within the first section. The housing may have a housing wall which delimits the housing opening and the first section may contact the housing wall. The housing may define a longitudinal axis and two second sections may be situated coaxially to the longitudinal axis as seen in a sectional plane perpendicular to the longitudinal axis, the two second sections being separated by a first section, the longitudinal axis passing through a second section.

Within the scope of the present invention, deformation of a body is understood to mean a change in its shape due to the action of an external force. The deformation may manifest itself as a change in length, a change in angle, a change in size or a change in volume. The force of the body which opposes the external force is the deformation resistance. Correspondingly, the deformability indicates the degree of deformation under a certain application of force. Thus, bodies having a higher deformability as compared to bodies having a lower deformability oppose the external force with less deformation resistance, i.e., they are deformed with less expenditure of energy. The deformation is divided into plastic deformation or irreversible deformation and elastic deformation or reversible deformation.

An irreversible, i.e., a permanent, deformation is called plastic deformation. The property of a material associated therewith is called plasticity or ductility. In this case, a material must be deformable, i.e., having low brittleness.

A reversible, i.e., reversible or temporary, deformation on the other hand is called elastic deformation. The material property associated therewith is called elasticity. Thus, within the scope of the present invention, elasticity is understood to mean the property of a body or material to change its shape under application of force and to return to its original shape when the force is no longer applied. A higher elasticity means that, for the same deformation, for example in the form of an expansion or compression, less force, or for a stronger deformation, the same force, must be applied, as compared to a lower elasticity. The elasticity may, for example, be circumscribed by the elasticity modulus or the compression modulus. The compressibility is the reciprocal value of the compression modulus and describes this behavior. The smaller the compression modulus, the more easily compressible the material is.

Within the scope of the present invention, elastomers are understood to mean rigid, yet elastically deformable plastic materials. The elastomeric plastic materials may be elastically deformed under tensile and compressive load, but return to their original non-deformed shape when the load is eliminated.

Within the scope of the present invention, plasticizers are understood to mean substances which are added to plastics, dyes, lacquers, rubber, adhesives and film coatings, in order to render them softer, more flexible, more supple and more elastic when used or for further processing. Plasticizers shift the thermoplastic range of a plastic toward lower temperatures in such a way that the plastic has the desired "more elastic" properties, even in the range of the operating temperature.

The sensor may be designed, for example, as a finger-type sensor, thus, for example, as a lambda sensor having a tubular structure. Since the sensor may be employed in particular in the field of automotive engineering, the measuring gas space may in particular be an exhaust system of an internal combustion engine, and the gas in particular an exhaust gas. However, the present invention may also be used in connection with any type of sensor element or sensor in which a grommet must be sealed.

In the sensor according to the present invention, the material composition of the sealing body is not homogeneously distributed, but instead, for example, a gradient of the plasticizer concentration may exist. For example, the sealing body may be formed of fluororubber or perfluororubber having at least 60% by weight of fluorine. A plasticizer in the form of dioctylphthalate may be used. However, other low molecular compounds, for example, at a weight ratio of 0.5% to 5% by weight may be introduced into the polymer mass of the sealing body made of fluororubber or perfluororubber, so that the elastomeric properties may be influenced. Other commercially available plasticizers, such as adipic esters or sebacic esters may also be used, depending on the type of fluororubber. In particular, plasticizers containing fluorine, such as fluoroaromatics, fluoroalkanes or fluoropolyethers, may also be introduced up to 10% by weight into the base polymer matrix.

Thus, it is particularly advantageous to combine a preferably high proportion of plasticizers in the outer layers of the sealing body with preferably few plasticizers in the core of the sealing body. A high elasticity of the sealing edge layers is achieved with a low overall plasticizer proportion. A high elasticity of the sealing body surface is a prerequisite for a good seal between the boundary surfaces between the sealing body and the housing, and between the sealing body and the connection cable.

BRIEF DESCRIPTION OF THE DRAWINGS

Additional optional details and features of the present invention result from the following description of preferred exemplary embodiments, which are schematically shown in the figures.

DETAILED DESCRIPTION OF EXAMPLE EMBODIMENTS

Figure 1:
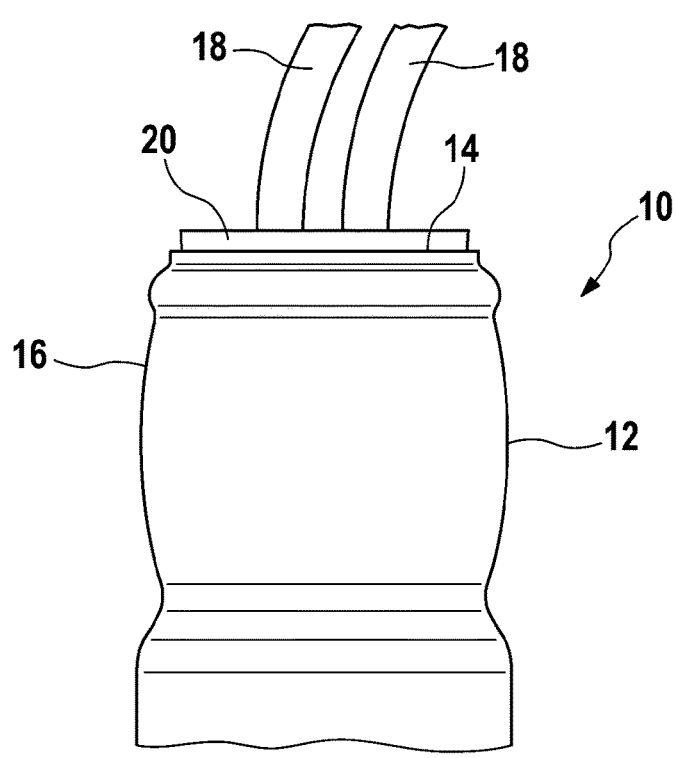
FIG. 1 shows a side view of a sensor in the area of a housing opening.

FIG. 1 shows a side view of a sensor 10. More precisely, FIG. 1 shows a part of a sensor 10. Sensor 10 is configured, for example, as a lambda sensor. The lambda sensor is used to control an air-fuel mixture of an internal combustion engine, in order, by measuring the concentration of the oxygen content in the exhaust gas, to be able to adjust a preferably stoichiometric mixture so that the pollutant emission is minimized as a result of a preferably optimal combustion. Hence, within the scope of the present invention the measuring gas space may be an exhaust system of an internal combustion engine. For this purpose, sensor 10 may project into the exhaust system. The lambda sensor is described below as an exemplary embodiment of a sensor for determining at least one physical and/or chemical property of a measuring gas, in particular the temperature or the concentration of a gas component, in particular in the exhaust gas of an internal combustion engine. The differences relative to conventional sensors in particular are described and the mode of operation is not discussed since this is well known, and since the mode of operation of the present invention does not differ.

Sensor 10 includes a housing 12 which has a housing opening 14. Housing opening 14 is delimited by a housing wall 16. At least one electrical connection cable 18 is led through housing opening 14. In the representation in FIG. 1, for example, two of a total of four connection cables 18 are apparent. Situated at least partly in the housing opening 14 is a sealing body 20, such as a grommet, for example. Sealing body 20 is provided in order to form a gastight and/or watertight seal of housing opening 14 so that gases and/or water are unable to penetrate into the interior of housing 12. Sealing body 20 may contact housing wall 16 in such a way that a gastight and/or watertight seal is also formed along housing wall 16. Extending through sealing body 20 are connection cables 18. Housing 12 is cylindrical or sleeve-like in design in the area of sealing body 20. In particular, housing 12 may be made of metal or an alloy in the area of sealing body 20. Sealing body 20 is fixed in housing opening 14 with the aid of caulking or deformation of housing 12.

Figure 2:
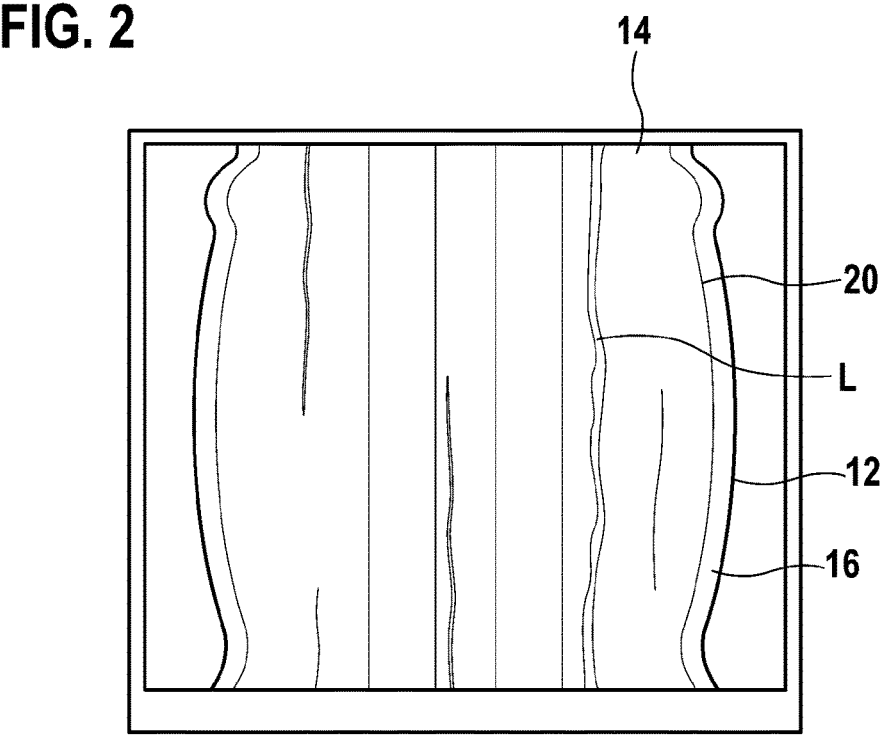
FIG. 2 shows an X-ray image of a sensor in the area of a housing opening.

If sealing body 20 would be made of an elastomeric material, such as fluororubber or perfluororubber having a homogeneous distribution of plasticizers, then leakage paths could form with the increasing age of sealing body 20 due to an excessive proportion of plasticizers. This would lead to concerns of gas or water penetrating into the interior of housing 12. FIG. 2 shows an X-ray image of housing 12 in the area of such an aged sealing body 20 in which a leakage path is clearly recognizable at the point indicated by L.

Figure 3:
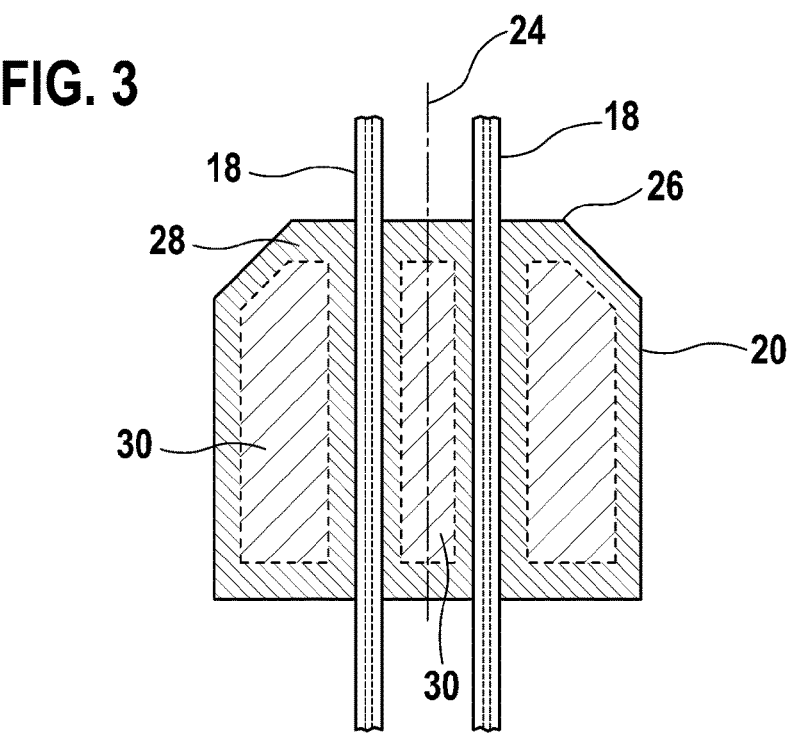
FIG. 3 shows a cross-sectional view of a sensor according to the present invention.

The present invention avoids such disadvantages. FIG. 3 shows an exemplary specific embodiment of the present invention. In particular, FIG. 3 shows a cross-sectional representation through sealing body 20. Extending through sealing body 20 are two or more connection cables 18, only two of which are visible in this representation. The number of connection cables led through may vary. In temperature sensors or unheated lambda sensors, for example, usually two cables are used, in heated binary and broadband lambda sensors three, four or five cables are used, and in special sensors, such as NOx sensors, six and more cables are used. Connection cables 18 are guided through through-holes 22 in sealing body 20, which run in parallel to a longitudinal axis 24 of housing 12. Sealing body 20 encloses connection cables 18 at least partially, the connection cables being fully enclosed in the circumferential direction, i.e., in a direction about the longitudinal axis, in the specific embodiment of sealing body 20 shown. In the exemplary specific embodiment of the present invention according to FIG. 3, sealing body 20 has a generally cylindrical shape, sealing body 20 having a cross-section taper at one axial end 26, at which point connection cables 18 exit sealing body 20 and which may be facing away from a housing interior. Sealing body 20 measures 9 mm, for example, in an axial direction, i.e., a direction parallel to longitudinal axis 24, and 12 mm in a radial direction, i.e., a direction perpendicular to longitudinal axis 24. The manufacturing tolerance of these dimensions may be 2 mm. It is understood that the respective dimensions of sealing body 20 may vary as a function of a variation in the dimensions of housing 12, so that, for example, in the case of a housing opening 14 having a larger diameter, sealing body 20 may have a correspondingly larger dimension in the radial direction.

Sealing body 20 has in particular a first section 28 and two second sections 30. First section 28 has a higher deformability, such as a higher elasticity, in particular higher compressibility, as compared to second sections 30. As shown in FIG. 3, two second sections 30 having lower elasticity are situated coaxially relative to the longitudinal axis 24 of housing 12, as seen in a sectional plane perpendicular to longitudinal axis 24, second sections 30 being separated by first section 28 having higher elasticity. One of two second sections 30 is situated in the center of sealing body 20 so that longitudinal axis 24 extends through a second section 30 having lower elasticity. Second section 30 having the lower elasticity is accommodated or embedded in first section 28 having the higher elasticity so that the surface of second section 30 having the lower elasticity is completely covered by first section 28 having the higher elasticity. Correspondingly, first section 28 forms the terminus of sealing body 20 outwardly both in the radial and axial direction. Output cables 18 extend in particular through first section 28 having higher elasticity. Here, the higher elasticity is achieved in that the material of first section 28 contains a higher proportion of plasticizer than the material of second section 30. In particular, a plasticizer having a dioctylphthalate content of 0.5% by weight to 15% by weight, preferably 0.25% by weight to 12.5% by weight, and even more preferably 0.5% by weight to 10% by weight may be introduced into the material of sealing body 20, for example, having a content of 5% by weight. Alternatively, adipic esters or sebacic esters may be used. Plasticizers containing fluorine, such as fluroaromatics, fluroalkanes or fluoropolyethers of up to 10% by weight may also be incorporated in the material of sealing body 20. A plastic may be used as material for sealing body 20, such as at least one elastomer, in particular fluororubber or perfluororubber having a fluorine content of at least 50% by weight, preferably at least 55% by weight and even more preferably at least 60% by weight for example, having a fluorine content of 65% by weight. Such fluororubbers contain, for example, 64% to 74% by weight of fluorine, 21% to 27% by weight of carbon black, and 7% by weight of miscellaneous unlisted components. Such fluororubbers include, for example, Viton® of DuPont Dow Elastomers, Tecnoflon® of Solvay Plastics, Fluorel® of Dyneon LLC, Daiel® of Daikin America, Inc., available for example through Datwyler Cables GmbH, Auf der Roos 4-12 65795 Hattersheim, Germany. Such perfluororubbers include, for example, Kalrez® of DuPont Dow Elastomers, Isolast of Trelleborg Sealing Solutions, Paroflour® of Parker Hannifin GmbH, HPF® of Quarzwerke GmbH, available for example through Datwyler Cables GmbH, Hattersheim, Germany, CTR (Chung Ta Rubber Co., Ltd.), Taiwan or Doosung Co. Ltd., Korea.

Figure 4:
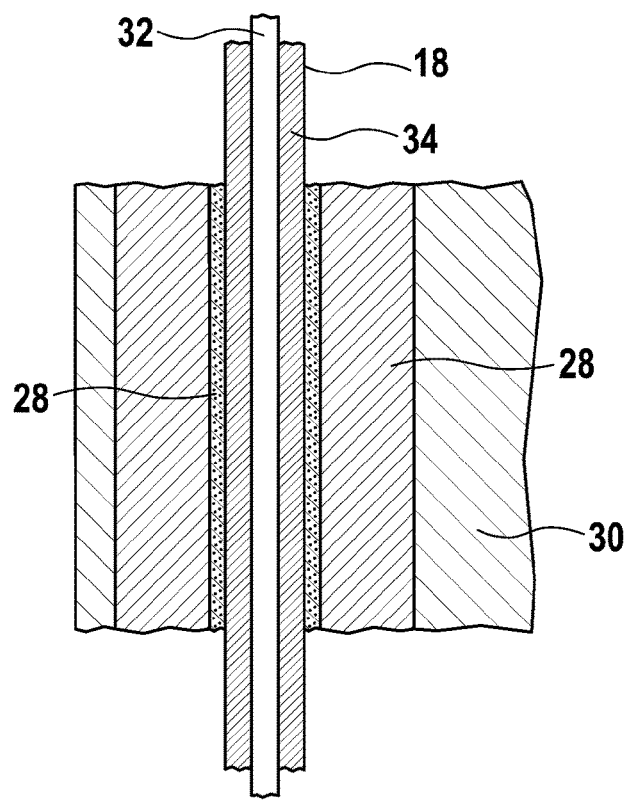
FIG. 4 shows an enlarged section of a sealing body in the area of the grommet.

FIG. 4 shows an enlarged section in the area of a through-hole 22 of an output cable 18. Output cable 18 includes a strand 32 as the actual electrical conductor, which may be made of copper and/or nickel, for example, and a sheathing 34 made of an electrically insulating material, such as polytetrafluoroethylene. The area between first section 28 having higher elasticity and sheathing 34 of output cable 18 may be filled with a layer of a viscous paste having, for example, 1% by weight to 10% by weight of a fluorine-containing plasticizer. In other words, in the space of a through-hole 24 remaining between an inner wall of the same and sheathing 34 such a paste may be introduced, for example, in the form of an adhesive. Alternatively, a single layer or multilayer tube having comparable mechanical, physical and chemical properties made of a fluorine-containing plastic may also be introduced into through-hole 24. As a result of the special design of a sealing body 20 according to the present invention, excellent sealing properties of the latter are achieved, in particular in the area around output cable 18, whereas a long-term stable property is also created due to second sections 30 having lower deformability, in particular, lower elasticity, since even during thermal aging not too much material is discharged from sealing body 20 due to volatilization of plasticizers, and the sealing body shrinks and/or becomes brittle to only a marginal degree.

In principle, fluorinated elastomers, such as the aforementioned fluororubbers or perfluororubbers, are used as a base material for sealing body 20. Due to their special temperature resistance and resistance to media, these materials are preferably used even beyond long operating lives, since they are able to meet the high temperature demands at an exit of output cable 18 from housing opening 14 of exhaust gas sensors. For example, these materials may ensure a thermal load at 300° C. for over 40 hours or at 250° C. for over 400 hours with reliable water and gas tightness. A sealing body 20 is constructed from such a fluorinated elastomer in multiple steps. Normally, such a fluororubber is used as a granulate, a granulate mix or as a mass and is prepared using known additives to create a viscous material. In principle, additional solid fillers, such as flame black for coloring or basic oxide may be introduced into the base material. Volatile plasticizers and other additives, such as dioctylphthalate, may also be introduced in the base material for improving processability. This viscous material is poured into a mold and via a pressing process, so-called compression molding, given the required geometry. Medium to long-chain polymers are particularly suitable for this process. Depending on the desired number of output cables 18, appropriate through-holes 24 may be provided by introducing thin rods into the press mold. These are then removed from the mold body after press molding, thereby providing through-holes 24 for output cables 18.

The varying elasticities of sections 28 and 30, i.e., the plasticizer gradient, in this example using plasticizers, may in principle be achieved through post-treatment, so-called curing. In the process, a thermally pre-aged sealing body 20 is subjected to a solution or gas phase containing a plasticizer. The thermal pre-aging, i.e., the so-called aging of the finished molded part at temperatures close to the maximum operating temperature, is a process crucial for ensuring consistent sealing body properties over the lifetime. Here, a cyclical aging may be preferable, i.e., a multiple heating to just below the maximum component operating temperature. Because sealing body 20 is subjected to the solution or gas phase containing the plasticizer, the solvent or the plasticizers are absorbed or deposited in the outer layers of sealing body 20 to thereby produce the desired plasticizer gradient in sealing body 20. In the example, the outer layers are the radial and axial external surfaces as well as the interior walls in the area of through-holes 24 for output cables 18. Alternatively, an even stronger gradient may be achieved by coating sealing body 20 with a plasticized adhesive. It is also possible for first section 28 and second section 30 to be made of the same plastic material, but to differ in terms of their elastomer contents. In particular, the sealing surfaces of sealing body 20, i.e., the surfaces which represent the contact surfaces with another component to be sealed off, may be coated with a thin layer of a plasticized adhesive. For example, only a partial coating of surfaces is possible, such as, for example, only the interior walls of through-holes 24 for output cables 18, which must take on particularly critical sealing tasks. Alternatively, sealing body 20 may also be composed of multiple components having the aforementioned properties. Several examples of manufacturing processes and specific embodiments are described in greater detail below, which achieve the aforementioned effects and implement the aforementioned embodiments.

A first variant of a manufacturing method for achieving the aforementioned elastic properties in the respective sections of sealing body 20 is, for example, in a first step to thermally age a single-piece sealing body 20 made of homogeneous fluororubber or perfluororubber. A cyclical heating is advantageous, in which, however, the maximum temperature, the hold time and the number of cycles are a function of the selected fluororubber or perfluororubber. For example, ten cycles at 250° C. with a hold time in each case of one hour or a temperature of 250° C. over several hours is preferred. In particular, the thermal aging may take place in an evacuable furnace, in which, for example, a number of cycles are carried out at normal pressure under normal atmosphere and another number of cycles under reduced pressure. In a second step, the surface of aged sealing body 20 is wetted in an immersion bath composed of a solvent and plasticizers. Here, the solvent and the plasticizers, the storage period and the temperature are selected in such a way that a swelling of the outer layers occurs, i.e., of the outer surfaces and the interior walls in the area of through-holes 24, while the core of sealing body 20 remains unaffected, since the plasticizers do not penetrate the deeper layers of sealing body 20. A mixture of the alcohols ethanol and isopropanol as the solvent with the plasticizer dioctylphthalate for a storage period of 24 hours may be used, for example, depending on whether it is fluororubber or perfluororubber. This process step may, for example, be carried out in an autoclave under increased pressure. Alternatively, a surface treatment in a gas atmosphere under pressure is also possible. In a third step, a sealing body 20 designed in this way is affixed in housing opening 14, for example by caulking.

As an alternative to these aforementioned manufacturing methods, a single-piece sealing body 20 made of a homogeneous fluororubber or perfluororubber may be thermally aged as in the first described variant. In a subsequent step, the outer layers of sealing body 20 are wetted with a viscous paste, such as an adhesive preparation, of a fluorine-containing plasticizer having, for example, 1% by weight to 10% by weight of fluorine. For example, the adhesive preparation is only partially applied by a metering unit to the interior walls in the area of through-holes 24 for output cables 18 which represent particularly critical sealing areas. Alternatively, a single layer or multilayer tube having comparable mechanical, physical and chemical properties made of fluorine-containing plastics may be introduced into through-holes 24. In a third step, sealing body 20 so designed is affixed to housing opening 14 as described above.

Figure 5:
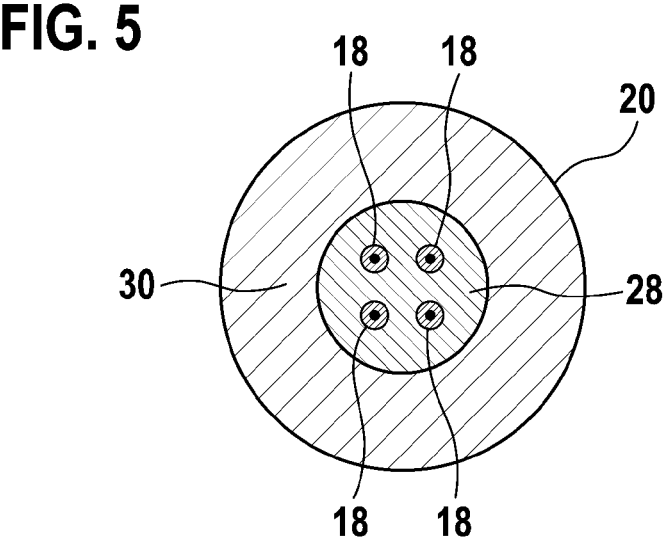
FIG. 5 shows a modification of the sealing body according to the present invention.

In a further variant, it is possible to design sealing body 20 as a multi-part component. In this case, the gradient of deformability, in particular elasticity, is already adjusted during the shaping of sealing body 20. Here, first section 28 having the higher deformability is formed as the core, the so-called pill, of sealing body 20 having through-holes 24 for output cables 18, on which the greatest demands with respect to elasticity and sealing action are placed, from a fluororubber or perfluororubber having a high plasticizer proportion in which the plasticizer or plasticizers are added already during the preparation of the rubber, i.e., even before the pouring of the rubber matrix into the molding tool for the compression molding. In a second shaping process, the core, i.e., first section 28, is encased by second section 30 having lower deformability, in particular elasticity, in the form of a ring made of a harder, i.e., less elastic, fluorinated or perfluororubber. Such a design is shown, for example, in FIG. 5, in which two or more output cables 18 are provided which are led through first section 28 having higher elasticity, second section 30 having lower elasticity being provided coaxially relative to first section 28 having higher elasticity. Thereafter, sealing body 20 is thermally aged as in the first described variant, then affixed to or in housing opening 14.

Figure 6:
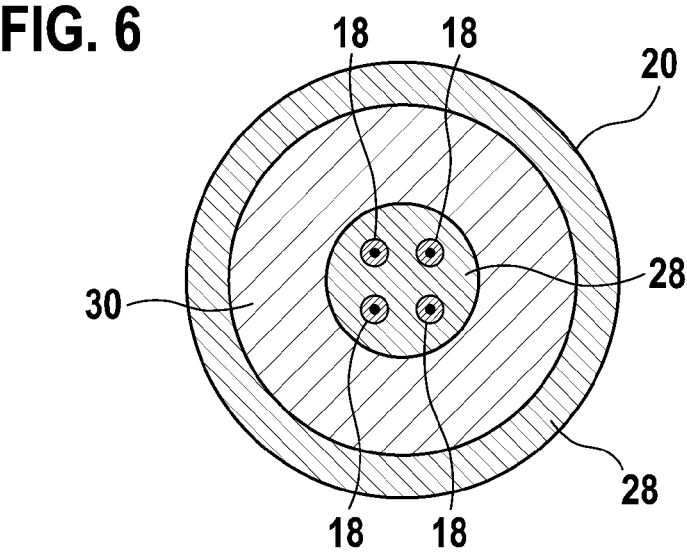
FIG. 6 shows another modification of the sealing body according to the present invention.

Alternatively, a three-part design of sealing body 20 is also possible. FIG. 6 shows such a design, in which sections 28 and 30 are provided in coaxial arrangement, first sections 28 having higher elasticity being separated by a second section 30 having lower elasticity. Such a multi-part sealing body 20 may result in high design costs, however, as a result of added complexity to the pressing process.

It is expressly emphasized that all features disclosed in the description should be considered separately and independently of one another for the purpose of the original disclosure, irrespective of the feature combinations in the specific embodiments. It is expressly noted that all range specifications or specifications of groups of units disclose every possible intermediate value or every possible subgroup for the purpose of the original disclosure, in particular also as a limit of a range specification.

What is claimed is:
1. A sensor, comprising:
a housing including a housing opening;
at least one connection cable led, approximately parallel to a longitudinal axis of the housing, from the housing through the housing opening;

at least one sealing body, the sealing body enclosing at least partially the connection cable, the sealing body including at least one plastic material having at least one plasticizer and at least one first section and at least one second section, the first section having a higher deformability than the second section and a higher plasticizer proportion in the plastic material than the second section, the sealing body including a grommet, the at least one first section and at least one second section being situated together on at least one transverse cross section of the housing that is perpendicular to the longitudinal axis of the housing.

2. The sensor as recited in claim 1, wherein the sealing body is situated at least partially in the housing opening.

3. A sensor comprising:
a housing including a housing opening;
at least one connection cable led from the housing through the housing opening;
at least one sealing body, wherein:
the sealing body:
encloses at least partially the connection cable;
includes at least one first section and at least one second section;
includes a grommet; and
includes at least one plastic material having at least one plasticizer; and
the first section has a higher deformability than the second section and a higher plasticizer proportion in the plastic material than the second section.

4. The sensor as recited in claim 1, wherein the plastic material contains the at least one plasticizer having a content of 0.1% to 15% by weight.

5. The sensor as recited in claim 3, wherein the plastic material contains the at least one plasticizer having a content of 0.25% to 12.5% by weight.

6. The sensor as recited in claim 3, wherein the plastic material contains the at least one plasticizer having a content of 0.5% to 10% by weight.

7. The sensor as recited in claim 3, wherein the plastic material contains the at least one plasticizer having a content of 5% by weight.

8. The sensor as recited in claim 3, wherein the at least one plasticizer contains fluorine.

9. The sensor as recited in claim 3, wherein the plastic material includes at least one elastomer.

10. The sensor as recited in claim 9, wherein the elastomer is selected from the group composed of fluororubber and perfluororubber.

11. The sensor as recited in claim 10, wherein the elastomer is fluororubber having a fluorine content of at least 50% by weight.

12. The sensor as recited in claim 10, wherein the elastomer is fluororubber having a fluorine content of at least 55% by weight.

13. The sensor as recited in claim 10, wherein the elastomer is fluororubber having a fluorine content of at least 60% by weight.

14. The sensor as recited in claim 10, wherein the elastomer is fluororubber having a fluorine content of at least 65% by weight.

15. The sensor as recited in claim 10, wherein the elastomer is perfluororubber having a fluorine content of at least 50% by weight.

16. The sensor as recited in claim 15, wherein the elastomer is perfluororubber having a fluorine content of at least 55% by weight.

17. The sensor as recited in claim 15, wherein the elastomer is perfluororubber having a fluorine content of at least 60% by weight.

18. The sensor as recited in claim 15, wherein the elastomer is perfluororubber having a fluorine content of at least 65% by weight.

19. The sensor as recited in claim 1, wherein the first section surrounds the at least one connection cable.

20. The sensor as recited in claim 1, wherein the second section is situated coaxially relative to the first section.

21. A sensor comprising:
a housing including a housing opening;
at least one connection cable led from the housing through the housing opening;
at least one sealing body, wherein:
the sealing body encloses at least partially the connection cable and includes at least one first section and at least one second section situated within the first section;
the sealing body includes at least one plastic material having at least one plasticizer;
the first section has a higher deformability than the second section and a higher plasticizer proportion in the plastic material than the second section; and
the sealing body includes a grommet.

22. The sensor as recited in claim 1, wherein the housing has a housing wall which delimits the housing opening and the first section contacts the housing wall.

23. The sensor as recited in claim 1, wherein the housing defines a longitudinal axis and two second sections are situated coaxially to the longitudinal axis as seen in a sectional plane perpendicular to the longitudinal axis, the two second sections being separated by the first section, the longitudinal axis extending through a second section.

* * * * *